(12) United States Patent
Gonzalez et al.

(10) Patent No.: US 8,506,814 B2
(45) Date of Patent: Aug. 13, 2013

(54) PROCESS FOR MEMBRANE SEPARATION OF LINEAR HYDROCARBONS WITHIN A HYDROCARBON MIXTURE

(75) Inventors: Serge Gonzalez, Decines (FR); Jacques Vallet, Lyons (FR); Arnaud Baudot, Vernaison (FR); Helene Rodeschini, Lyons (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 714 days.

(21) Appl. No.: 12/376,807

(22) PCT Filed: Jul. 6, 2007

(86) PCT No.: PCT/FR2007/001173
§ 371 (c)(1),
(2), (4) Date: Jun. 30, 2010

(87) PCT Pub. No.: WO2008/017744
PCT Pub. Date: Feb. 14, 2008

(65) Prior Publication Data
US 2010/0276368 A1    Nov. 4, 2010

(30) Foreign Application Priority Data
Aug. 9, 2006  (FR) ................... 06 07277

(51) Int. Cl.
*B01D 61/36*   (2006.01)
*B01D 71/64*   (2006.01)
*B01D 71/32*   (2006.01)
*B01D 53/22*   (2006.01)

(52) U.S. Cl.
USPC ............ 210/640; 95/50; 95/45; 210/651; 210/500.39; 210/500.38; 210/500.4; 210/500.41

(58) Field of Classification Search
None
See application file for complete search history.

(56) References Cited

U.S. PATENT DOCUMENTS

| | | | | |
|---|---|---|---|---|
| 4,988,371 A * | 1/1991 | Jeanes et al. | ............... | 95/53 |
| 5,076,816 A * | 12/1991 | Avrillon et al. | ............... | 95/51 |
| 5,290,452 A | 3/1994 | Schucker | | |
| 5,352,272 A * | 10/1994 | Moll et al. | ............... | 96/9 |
| 5,409,525 A | 4/1995 | Kazama et al. | | |
| 5,837,032 A * | 11/1998 | Moll et al. | ............... | 95/45 |
| 6,531,569 B1 | 3/2003 | Tachiki et al. | | |
| 6,899,743 B2 | 5/2005 | Wijmans | | |
| 2003/0233934 A1* | 12/2003 | Wijmans et al. | ............... | 95/46 |
| 2007/0137485 A1* | 6/2007 | Bitterlich et al. | ............... | 96/11 |
| 2009/0032465 A1* | 2/2009 | Baumgarten et al. | ......... | 210/637 |

FOREIGN PATENT DOCUMENTS

| | | |
|---|---|---|
| EP | 0 412 882 A | 2/1991 |
| EP | 0 545 686 A | 6/1993 |

OTHER PUBLICATIONS

International Search Report, PCT/fr2007/001173, Nov. 14, 2007, 2 pages, Thomas Eikenboom, Nov. 30, 2007.
Islam et al. "Preparation and gas separation performance of flexible pyrolytic membranes by low-temperature pyrolysis of sulfonated polymides", 'Journal of Membrane Science', Sep. 15, 2005, pp. 17-26, vol. 261, Elsevier Scientific Publ. Company, Amsterdam, NL.

* cited by examiner

*Primary Examiner* — Krishnan S Menon
(74) *Attorney, Agent, or Firm* — Millen, White, Zelano & Branigan, P.C.

(57) ABSTRACT

The invention relates to a process for membrane separation that makes it possible to separate linear hydrocarbons from branched hydrocarbons. The membrane that is used comprises a dense selective layer that consists of a polymer whose chemical structure contains at least one bis-phenyl-9,9-fluorene group.

19 Claims, No Drawings

US 8,506,814 B2

PROCESS FOR MEMBRANE SEPARATION OF LINEAR HYDROCARBONS WITHIN A HYDROCARBON MIXTURE

FIELD OF THE INVENTION

The invention relates to a process that makes it possible to separate linear hydrocarbons from branched hydrocarbons by means of a membrane that comprises a dense selective layer that consists of a polymer whose chemical structure contains a bis-phenyl-9,9-fluorene group.

This invention is particularly suitable for the separation of linear isomers and branched isomers.

This invention also applies to the separation of paraffin-type isomers or olefin-type isomers.

This invention finds a particularly advantageous application in the separation of a fraction of normal paraffins contained in a hydrocarbon fraction with a number of carbon atoms that ranges from 4 to 16, and more particularly with a number of carbon atoms that ranges from 4 to 10, and, for example, for a number of carbon atoms that is equal to 4, 5, or 6.

EXAMINATION OF THE PRIOR ART

In the documents of the prior art, the separation performance levels of the membranes are generally described by means of two parameters: permeability and selectivity.

Permeability is defined as the flow density of material that passes through the membrane, added to the thickness of said membrane and to the partial pressure difference of the compounds that pass through the membrane applied between the upstream and downstream faces.

The selectivity of the membrane for the component A relative to the component B is defined as the ratio of the permeabilities of the two components A to B.

The permeability is measured in barrers (1 barrer=$10^{-10}$ $cm^3 \cdot cm/cm^2 \cdot cm_{Hg}$, or in SI unit 0.75 $10^{-15}$ $Nm^3 \cdot m/m^2 \cdot s \cdot Pa$).

In the case of the separation of a binary mixture, the separation factor can be calculated in two ways: either from permeabilities that are obtained in pure objects (ideal selectivity or permselectivity is then the term used) or from data on the flows in a mixture (mixture selectivity or separation factor is then the term used).

The separation process that is described in this invention is carried out by a solution/diffusion mechanism through a dense polymer film that forms the selective layer of the membrane.

In general, the membranes that offer a high level of selectivity are not very permeable, and conversely, a very permeable membrane generally has selectivity values that are quite low.

The separation of molecules with a close boiling point or of a number of close carbon atoms is frequently used in refining and applies to various petroleum fractions.

The molecules that are concerned are most often paraffins of various degrees of branching and, to a lesser extent, olefinic compounds. More generally, this invention applies to the separation of isomers, regardless of the chemical family to which these isomers belong. Most often, it will be a matter of paraffinic isomers, or olefinic isomers.

These separations are generally carried out by distillation, by adsorption or according to the so-called simulated counter-current technique, and they have all of the well-known drawbacks in terms of energy costs or ease of operation.

The membrane separation technique is much less common in refining, but offers certain advantages, in terms of modularity, low energy consumption compared to conventional distillation, reduced maintenance costs because of the absence of moving elements, and the ability to carry out difficult separations.

The mineral membranes that are based on molecular sieves are the most common for carrying out the separation of isomer mixtures.

Thus, the U.S. Pat. No. 5,914,434 has a carbon membrane for separating the linear alkanes from the branched alkanes according to a diffusional selectivity mechanism.

The MFI-type zeolite membranes are most commonly cited in the literature. These zeolite membranes are selected primarily because the diameter of the micropores (on the order of 5.5 angstroms) is greater than the minimum kinetic radius of the linear paraffins (and especially linear olefins), which makes possible a rapid diffusion of this type of molecule, while being less than that of the paraffinic isomers or monobranched olefinic isomers, and especially multi-branched isomers, which will clearly diffuse more slowly than their linear homologs.

In addition, the zeolites are sieves that offer increased resistance to high temperatures and in the presence of organic compounds, which makes it possible to use this type of membrane in coupling with high-temperature reactors used in the refining industry.

Most of the R&D work in the field of zeolite membrane synthesis has aimed at producing the finest possible integrated zeolite layer. To our knowledge, the zeolite membrane that offers the finest selective layer (0.5 μm of thickness) that has been the object of a publication is described in an article by Hedlund et al. (Jonas Hedlund, Johan Sterte, Marc Anthonis, Anton-Jan Bons, Barbara Carstensen, Ned Corcoran, Don Cox, Harry Deckman, Wim De Gijnst, Peter-Paul de Moor, Frank Lai, Jim McHenry, Wilfried Mortier, Juan Reinoso, Jack Peters, *Microporous and Mesoporous Materials* 52 (2002) 179-189). The title of the journal cited can be translated into French by "matériaux microporeux et mésoporeux."

Because of the solid behavior of this type of zeolite film, it is necessary to carry out the synthesis of the selective zeolite layer on a porous substrate, most often metal or based on oxides (generally alumina).

Despite the advantages that are theoretically offered by the zeolite membranes, an in-depth analysis of the scientific literature shows that this type of material presents significant drawbacks:

(1) The difficulty of obtaining or maintaining a selected layer without intercrystalline defects during temperature separation tests
(2) Their reactivity in particular in the presence of reactive compounds such as olefins
(3) The difficulty of synthesizing thin layers on a large scale, because of the "discrete" nature of the zeolite crystals that constitute the selective layer
(4) The high cost of the metal or mineral substrates Relative to the first drawback, numerous authors, for example Stuart M. Holmes, Christian Markert, Richard J. Plaisted, James O. Forrest, Jonathon R. Agger, Michael W. Anderson, Colin S. Cundy, and John Dwyer, *Chem. Mater.* 1999, 11, 3329-3332 (translation of the title of the journal cited "Matériaux chimiques [Chemical Materials]"), have shown that intercristalline cracks appear during the calcination of the zeolite layer after synthesis or because of the expansion difference between the porous substrate and the selective zeolite layer.

These defects, particularly when the temperatures are high, can greatly alter the selectivity of the zeolite membranes. Numerous authors including Vu Anh Tuan, John L. Falconer, and Richard D. Noble, *Ind. Eng. Chem. Res.* 1999, 38, 3635-3646 (translation of the title of the journal cited "Recherche en génie chimique") have thus been able to observe that if the MFI-type zeolite membranes generally offered high mixture selectivities for the separation of the normal butane/isobutane mixture at low temperatures, the selectivity could greatly decrease with the temperature. Thus, the selectivities of MFI-type zeolite membranes at a temperature of more than 100° C. are generally quite reduced, as described in Table No. 1.

TABLE No. 1

Data Published in the Literature on Normal Butane/Isobutane Selectivities of ZSM-5-Structure Zeolite Membranes at High Temperatures.

| Nature of a Selective Layer | Separation Test Temperature | Mixture Selectivity | Reference |
| --- | --- | --- | --- |
| ZSM-5 | 200° C. | 4.8 | Tuan et al., 1999 |
| ZSM-5 | 200° C. | 5.2 | Tuan et al., 1999 |
| ZSM-5 | 130° C. | 2.8 | Bernal et al., 2002 |
| ZSM-5 | 130° C. | 3 | Bernal et al., 2002 |
| ZSM-5 | 130° C. | 13.4 | Bernal et al., 2002 |
| ZSM-5 | 150° C. | 2.5 to 4 | Jareman et al., 2003 |
| ZSM-5 | 150° C. | 5 | Nishiyama et al., 2001 |
| Na-ZSM-5 | 200° C. | 2 | Aoki et al., 2000 |
| H-ZSM-5 | 200° C. | 1.5 | Aoki et al., 2000 |
| Ca-ZSM-5 | 200° C. | 2 | Aoki et al., 2000 |
| K-ZSM-5 | 200° C. | 2 | Aoki et al., 2000 |
| Ba-ZSM-5 | 200° C. | 2.5 | Aoki et al., 2000 |
| ZSM-5 | 160° C. | 3 | Hedlund et al., 2002 |
| ZSM-5 | 150° C. | 10 | Coronas et al., 1998 |

The second drawback of the zeolite membranes relates to their reactivity, in particular in the presence of reactive compounds such as olefins. Actually, it is known to one skilled in the art that most of the zeolites contain aluminum that imparts an acidic nature to the microporosity of the zeolite.

The reactivity of the aluminum atoms in the network of the zeolite generally ultimately leads to a clogging of the pores of the zeolite by oligomerization of the olefins within.

This phenomenon becomes more pronounced as the mixture to be separated contains isobutene-type compounds.

More generally, the difficulty of synthesizing thin layers on a large scale, because of the "discrete" nature of the zeolite crystals that constitute the selective layer, combined with the high cost of the porous metal or mineral substrates that are necessary for maintaining the selective layer of the membranes based on the molecular sieve, are why this type of membrane has not experienced the anticipated industrial development. Actually, a single firm, Mitsui, continues the production of separation units based on small zeolite membranes (surface area of less than 100 $m^2$), whereas another, the Swiss company Sulzer, abandoned the production of mesoporous silica-based membranes because of their poor temperature behavior.

Unlike zeolites, polymers have numerous assets, in particular in terms of shaping. Actually, numerous polymers can be put into the form of very thin dense film. This capacity has been used since the 1970s to produce permanent gas separation membranes, and companies have developed a specialty in producing gas separation membranes in the form of hollow fibers with a very small diameter, which would make it possible to offer extremely compact membrane separation equipment.

The current applications for this type of membrane are:
Nitrogen/oxygen separation from air
Purification of hydrogen
$CO_2/CH_4$ separation in the natural gas industry Very few documents of the prior art refer to the use of polymer membranes for the separation of a hydrocarbon mixture. Actually, it is generally admitted by one skilled in the art that the hydrocarbons cause swelling phenomena of the polymer matrices that then lose their sieving properties, which is reflected in general by very low selectivities. As a result, there are not very many elements of the prior art that refer to the separation of a mixture of organic compounds comprising at least 4 carbon atoms.

It is possible to cite the U.S. Pat. No. 6,899,743 in which it is shown that it is possible to separate a mixture of normal butane and isobutane through a dense film made of Hyflon AD60x, a fluorinated polymer that is produced by the Solvay Company. The film has a permeability with regard to the normal butane that is higher than for isobutane. However, it clearly appears that the selectivity of the separation very greatly decreases with the temperature.

TABLE 2

Data on Normal Butane/Isobutane Selectivity on Dense Membranes Based on Hyflon AD 60x (Patent U.S. 6,899,743).

| Temperature | n-Butane/Isobutane Selectivity |
| --- | --- |
| 20° C. | 8.9 |
| 40° C. | 6.9 |
| 60° C. | 5.6 |
| 80° C. | 4.3 |

Within the scope of this invention, it was discovered, surprisingly enough, that the polymers whose molecular pattern comprised a bis-phenyl-9,9-fluorene group made it possible to very effectively separate the linear paraffins or olefins from branched paraffins or olefins. The linear compounds/branched compounds selectivities that were observed with the polymer-based films described in this invention are higher than those published in the literature, just like their permeability in relation to the linear compounds.

SUMMARY DESCRIPTION OF THE INVENTION

This invention belongs to the field of the processes for membrane separation and applies to the separation of linear hydrocarbons contained in a mixture of linear hydrocarbons and branched hydrocarbons.

For example, this process makes it possible to separate the normal butane from a mixture that contains other C4 hydrocarbons such as isobutane.

For example, this process makes it possible to separate the normal butenes from a mixture that contains other C4 hydrocarbons such as isobutenes.

It is shown in this invention that the presence of a particular group such as bis-phenyl-9,9-fluorene in a rigid polymer that is put into the form of dense film leads to superior separation properties, in particular in terms of the permeability of said film in relation to linear hydrocarbons, while maintaining a high linear compound/branched compound selectivity.

More generally, the process according to this invention applies to the separation of a fraction of normal paraffins or normal olefins, contained in a hydrocarbon fraction with a number of carbon atoms ranging from 4 to 16, and more particularly to the number of carbon atoms ranging from 4 to 10. In a particularly preferred manner, the process according to the invention applies to the separation of normal paraffins or normal olefins with 4, 5 or 6 carbon atoms. Hereinafter, the different cases depicted will be consolidated by referring to the separation of linear hydrocarbons with 4, 5 or 6 carbon atoms.

The membranes that are used in the process according to this invention are vitreous amorphous polymer-type membranes or have a low crystallinity that comprises, in the repetition pattern, at least one bis-phenyl-9,9-fluorene group.

The invention therefore consists of a process for membrane separation in which the selective layer of the polymer membrane consists of a dense polymer film whose chemical structure contains a bis-phenyl-9,9-fluorene group.

The selective layer of the polymer membrane that contains the bis-phenyl-9,9-fluorene group is selected from the group that consists of the polymers of the following families: the polyimides, the polyamides, the polycarbonates, the polysulfones, the poly(amide imides), the poly(ether sulfones), the polyesters, or the copolymers or mixtures of polymers of these families.

Preferably, the selective layer of the polymer membrane that contains the bis-phenyl-9,9-fluorene group belongs to the family of polyamides.

Also preferably, the selective layer of the polymer membrane that contains the bis-phenyl-9,9-fluorene group belongs to the family of polycarbonates.

Even more preferably, the selective layer of the polymer membrane that contains the bis-phenyl-9,9-fluorene group belongs to the family of polyimides.

DETAILED DESCRIPTION OF THE INVENTION

This invention belongs to the field of processes for membrane separation and applies to the separation of linear hydrocarbons that are contained in a mixture of linear hydrocarbons and branched hydrocarbons.

For example, this process makes it possible to separate the normal butane from a mixture that contains other C4 hydrocarbons such as isobutane.

For example, this process makes it possible to separate the normal butenes from a mixture that contains other C4 hydrocarbons such as isobutenes.

It is shown in this invention that the presence of a particular bis-phenyl-9,9-fluoroene-type group in a rigid polymer that is put into the form of dense film leads to superior separation properties, in particular in terms of permeability of said film in relation to linear hydrocarbons, while maintaining a high linear compound/branched compound selectivity.

More generally, the process according to this invention applies to the separation of a fraction of normal paraffins or normal olefins contained in a hydrocarbon fraction with a number of carbon atoms that ranges from 4 to 16, and more particularly with a number of carbon atoms that ranges from 4 to 10. In a particularly preferred manner, the process according to the invention applies to the separation of linear hydrocarbons with 4, 5 or 6 carbon atoms.

The membranes that are used in the process according to this invention are membranes of the polymer type that are amorphous, vitreous, or have low crystallinity, comprising, in the repetition pattern, at least one bis-phenyl-9,9-fluorene group.

The invention therefore consists of a process for membrane separation in which the selective layer of the polymer membrane consists of a dense polymer film whose chemical structure contains a bis-phenyl-9,9-fluorene group.

The selective layer of the polymer membrane that contains the bis-phenyl-9,9-fluorene group is selected from the group that consists of the polymers of the following families: the polyimides, the polyamides, the polycarbonates, the polysulfones, the poly(amide imides), the poly(ether sulfones), the polyesters, or the copolymers or polymer mixtures of these families.

In a first variant of the invention, the selective layer of the polymer membrane that contains the bis-phenyl-9,9-fluorene group belongs to the family of polyimides.

In a second variant of the invention, the selective layer of the polymer membrane that contains the bis-phenyl-9,9-fluorene group belongs to the family of polyamides.

In a third variant of the invention, the selective layer of the polymer membrane that contains the bis-phenyl-9,9-fluorene group belongs to the family of polycarbonates.

In a fourth variant of the invention, the selective layer of the polymer membrane that contains the bis-phenyl-9,9-fluorene group belongs to the family of polysulfones.

In a fifth variant of the invention, the selective layer of the polymer membrane that contains the bis-phenyl-9,9-fluorene group belongs to the family of poly(amide imides).

In a sixth variant of the invention, the selective layer of the polymer membrane that contains the bis-phenyl-9,9-fluorene group belongs to the family of poly(ether sulfones).

In a seventh variant of the invention, the selective layer of the polymer membrane that contains the bis-phenyl-9,9-fluorene group belongs to the family of polyesters.

Very preferably, the selective layer of the polymer membrane that contains the bis-phenyl-9,9-fluorene group belongs to the family of polyimides.

The polymer that constitutes the selective layer of the membrane can be a homopolymer, a copolymer, or a mixture of polymers.

The membranes that are used in this invention, in addition to the presence of the vitreous polymer that comprises at least one bis-phenyl-9,9-fluorene group in the repetition pattern, can contain mineral and organic feedstocks and additives that are intended to bring about, by virtue of their presence, an improvement in the separation factor and/or promote permeability. By way of example, it will be possible to cite the mineral feedstocks such as the inorganic salts, the zeolites, the clays, the mesoporous compounds, the native or post-treated silicas, the carbon blacks, the pyrolyzed polymers, the carbon nanotubes, and the dendrimers.

The membranes that are used in this invention, in addition to the presence of the vitreous polymer that comprises at least one bis-phenyl-9,9-fluorene group in the repetition pattern, can contain cross-linking agents that bring about an improvement in the separation factor and/or promote permeability.

The membranes that are used in this invention can be treated chemically, thermally, or by radiation for the purpose of improving the separation factor and/or promoting permeability.

In the repetition pattern, the polymer that constitutes the selective layer of the membrane according to the invention comprises at least one bis-phenyl-9,9-fluorene group of the general chemical formula:

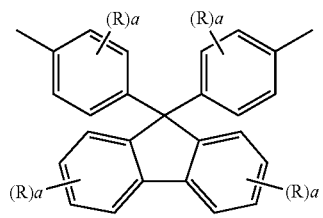

in which each of the groups R represents either a linear or branched alkyl group that has 1 to 16 carbon atoms, or a linear or branched alkoxy group that has 1 to 16 carbon atoms. For each of the groups R and independently from one group to the next, the index a can assume either the value of zero or a whole number between 1 and 4. Each value of the index a preferably will be 0 or 1.

Even more preferably, the index a will have a value of zero, which comes down to the elimination of the groups R.

For the alkyl groups, it is possible to cite in a nonlimiting manner the groups methyl, ethyl, propyl, isopropyl, and the linear or branched butyl groups.

For the alkoxy groups, it is possible to cite in a nonlimiting manner the groups methoxy, ethoxy, propyloxy, and the linear or branched butyloxy groups.

In a preferred version, the polymer that constitutes the selective layer of the membrane will be a homopolymer or a copolymer of general formula:

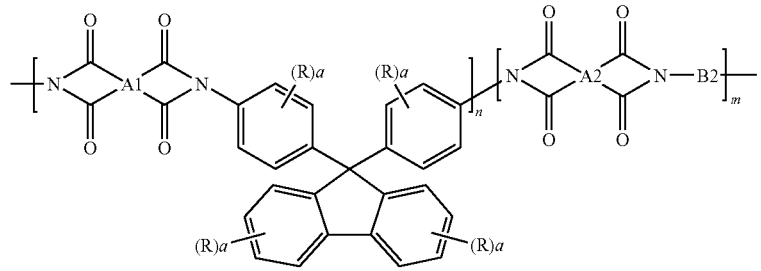

where A1 and A2 are hydrocarbon-containing tetravalent organic groups that are selected from among aromatic, alicyclic and aliphatic hydrocarbon groups, and the group B2 is a hydrocarbon-containing bivalent organic group that is selected from among the aromatic, alicyclic and aliphatic hydrocarbon groups. The indices m and n represent a positive whole number that corresponds to the degree of polymerization.

In a preferred version, the polyimide that constitutes the selective layer of the membrane is a statistical, alternate, sequenced or block polymer.

The method most generally used for obtaining the polyimide that constitutes the selective layer of the membrane results from the chemical reaction between
   a diamine that comprises in its structure the bis-phenyl-9,9-fluorene group of general formula:

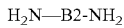

and a dianhydride of general formula:

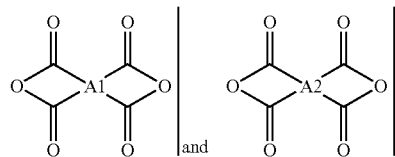

Within the scope of the invention, it will be possible to use a precursor, such as, for example, a tetra-carboxylic acid or the hemiester of a tetra-carboxylic acid.

Within the scope of the invention, the diamine can be selected from the following list:
   1,4-Diamino-2,3,5,6-tetramethylbenzene
   bis(4-Aminophenyl)ether
   2,4-Diamino-1-isopropylbenzene
   The diaminoanthraquinones
   2,7-Diaminofluorene
   4,4'-Diamino-3,3'-dimethoxybiphenyl
   2,4-Diaminotoluene
   Diaminodiphenylsulfone
   bis[4-(4-Aminophenoxy)phenyl]sulfone
   9,10-bis(4-Aminophenyl)anthracene
   1,4-bis(4-Aminophenyl)benzene
   bis(4-Aminophenyl)methane
   bis(4-Amino-3-ethylphenyl)methane
   bis(4-Amino-3-methylphenyl)methane
   bis(4-Amino-3-chloro-phenyl)methane
   bis(4-Aminophenyl)sulfide
   2,2-bis(4-Amino-3-hydroxyphenyl)propane
   4,4'-Diamino-3,3'-dichlorobiphenyl
   4,4'-Diamino-3,3'-dihydroxybiphenyl
   4,4'-Diaminobiphenyl
   9,9-bis(4-Aminophenyl)fluorene
   bis(4-Amino-2,6-methylphenyl)methane
   1,4-Diamino-2,5-dichlorobenzene
   1,4-Diamino-2,5-dimethylbenzene
   1,3-Diamino-2,4,6-trimethylbenzene
   bis(3-Aminopropyl)tetramethyldisiloxane
   2,5-Diaminopyridine
   4,4'-Diaminobenzanilide
   1,5-Diaminonaphthalene
   1,3-Diamino-5-trifluoromethylbenzene
   4,4'-Diamino-3,3',5,5'-tetramethylbiphenyl
   3,3'-Diamino-4,4'-dihydroxybiphenyl
   1,3-Phenylenediamine
   1,4-Phenylenediamine
   1,4-bis(4-Aminophenoxy)benzene.
   Preferably, the diamines will be selected from the following list:
   1a 1,4-Diamino-2,3,5,6-tetramethylbenzene
   9,9-bis(4-Aminophenyl)fluorene
   1,3-Diamino-2,4,6-trimethylbenzene
   bis(3-Aminopropyl)tetramethyldisiloxane.
   Within the scope of the invention, the dianhydride that is selected can be selected from the following list:
   bis(3,4-Dicarboxyphenyl)sulfonic acid dianhydride
   2,2-bis(3,4-Dicarboxyphenyl)hexafluoropropanoic acid dianhydride
   1,1-bis(3,4-Dicarboxyphenyl)ethanoic acid dianhydride
   Pyromellitic anhydride
   2,3,6,7-Naphthalenetetracarboxylic acid dianhydride
   3,3',4,4'-Biphenyltetracarboxylic acid dianhydride
   1,2,5,6-Naphthalenetetracarboxylic acid dianhydride
   2,2',3,3'-Biphenyltetracarboxylic acid dianhydride
   3,3',4,4'-Benzophenonetetracarboxylic acid dianhydride
   Oxydiphthalic acid dianhydride
   1,4,5,8-Naphthalenetetracarboxylic acid dianhydride 2,2-bis(3,4-Dicarboxyphenyl)propanoic acid dianhydride
3,4,9,10-Perylentetracarboxylic acid dianhydride
1,1-bis(2,3-Dicarboxyphenyl)ethanoic acid dianhydride
bis(2,3-Dicarboxyphenyl)methanoic acid dianhydride
bis(3,4-Dicarboxyphenyl)methanoic acid dianhydride.

The dianhydride will preferably be selected from the following list:
2,2-bis(3,4-Dicarboxyphenyl)hexafluoropropanoic acid dianhydride
Pyromellitic anhydride
3,3',4,4'-Biphenyltetracarboxylic acid dianhydride
3,3',4,4'-Benzophenonetetracarboxylic acid dianhydride.

The solvents that are necessary to the implementation of the polymerization can be selected from the following list:
N,N-Dimethylformamide
N,N-Diethylformamide
N,N'-Dimethylacetamide (DMAC)
N,N-Diethylacetamide
N-Methyl-2-pyrrolidone (NMP)
N-Cyclohexyl-2-pyrrolidone
Phenol
o-, m-, p-cresol
Xylenol
Halogenated phenols
Catechol
Hexamethylphosphoramide
Dimethylpropyl urea
Benzyl alcohols
Lactates
Lactones such as γ-butyrolactone.

The solvents will preferably be selected from the following list:
N,N-Dimethylacetamide (DMAC)
N-Methyl-2-pyrrolidone (NMP)
o-, m-, p-cresol
Lactones such as γ-butyrolactone.

These solvents can be used alone or in a mixture.

The knowledge of the molecular weight of the polymer is not essential, and it will be preferable to follow the evolution of the inherent viscosity of the polymer that should be at least more than 0.1 dl/g and preferably between 0.3 dl/g and 2 dl/g. The inherent viscosity is defined relative to a reference viscosity and to the concentration of the polymer in solution in the solvent. Its value is homogeneous, unlike said concentration, i.e., 1 dl/g (=0.1 m$^3$/kg).

Most of the polymers that are being considered in this invention for an implementation in membrane form are soluble in a large variety of common organic solvents including most of the aprotic solvents, which are generally used for the formation of polymer membranes such as NMP.

The polymer membrane that contains the bis-phenyl-9,9-fluorene group can be homogeneous or asymmetrical.

The polymer that constitutes the selective layer of the membrane can be used in the form of film or fibers according to the known techniques of one skilled in the art.

Once synthesized, the polymer in the form of a solid is dissolved in a suitable solvent such as NMP, for example, with a polymer content on the order of 1% to 50% by weight, and preferably between 5 and 20% by weight.

The solution is extended in film form with the desired thickness on a flat substrate or on a substrate that comes in the form of hollow fibers, or else it is extruded through a conventional spinner.

It is possible to produce the membrane, and composite membrane will then be the term used, by depositing a polymer film that comprises in its chain at least one bis-phenyl-9,9-fluorene group with a thickness of between 0.05 and 1 micron (1 μm=10$^{-6}$ meter) on a substrate that was previously used in the form of hollow fibers.

The substrate advantageously will be selected so that it offers the advantage of being much more permeable than the polyimides in general and does not contribute significantly to the resistance to the transfer of material through the resulting composite membrane.

According to an embodiment of the invention, the substrate will be a porous layer or a hollow fiber that consists of a polymer material such as, for example, a polysulfone, a polyethersulfone, a polyetherimide, a vinylidene polyfluoride, a polyethylene or a polypropylene, a polyacrylonitrile, a polyimide, a phenylene polyoxide, or a polymer derivative of cellulose, such as a cellulose acetate or an ethyl cellulose. The substrate can be a polymer that consists of different organic or mineral materials.

The adhesion between the selective layer and the substrate in some cases requires physical or chemical treatments that are well known to one skilled in the art.

Hereinafter, the separation of normal butane contained in a mixture of normal butane and isobutane will be taken as an example. It should be kept in mind, however, that this process applies as well to the separation of the butene-1 from a mixture that contains other hydrocarbons such as isobutene.

The membranes of this invention can be used in various types of modules intended for the production of the separation unit. The final separation module can consist of one or more membranes. The module can be assembled with other identical modules so as to form a separation unit that has the desired size.

During operation, the feedstock that consists of a mixture of linear and branched hydrocarbons is brought into contact with one of the sides of the membrane.

Hydrocarbon feedstock is defined preferably within the scope of this invention as the paraffins or the olefins that comprise at least 4 carbon atoms.

By imposing a pressure difference between the side of the feedstock and the permeate side, the linear compounds pass through the membrane at a higher speed than the branched compounds that comprise the same number of carbon atoms. This difference in speed produces a hydrocarbon flow that is enriched with linear compounds, which is sampled from the permeate side of the membrane.

This invention is not intended only for gas phase separations but can be extended to other types of separation, in liquid phase, for example, for temperature and pressure conditions that cover a large field of use. In addition, the separation can take place for mixtures that contain more than two components.

Broadly speaking, the process for membrane separation according to the invention operates at a temperature of between 40 and 250° C., for pressures of between 0.1 MPa and 5 MPa (1 bar=0.1 MPa).

Preferably, the process for membrane separation according to the invention operates at a temperature of between 40 and 200° C. for pressures of between 1 bar and 40 bar. Even more preferably, the process for membrane separation according to the invention operates at a temperature of between 50 and 150° C., for pressures of between 0.1 MPa and 2 MPa.

EXAMPLES ACCORDING TO THE INVENTION

Example 1 (According to the Invention)

The polymer 6FDA-BDAF that is the object of Example 1 is the result of polycondensation of the 2,2-bis(3,4-dicarboxyphenyl)hexafluoropropanoic acid dianhydride (6FDA) and the 9,9'-bis-(4-aminophenyl)-fluorene (BDAF) in an equimolar mixture. After purification of the monomers by recrystallization in appropriate solvents, the polycondensation of the polyimide is carried out in two stages: in a first step, the acid polyamide is produced, but the polyimide is obtained in a second cyclization stage by a chemical method.

During the first polymerization stage, the mixing of the dianhydride and the diamine is carried out under inert atmosphere and in an anhydrous environment in the N,N-dimethylacetamide solvent (DMAC).

The cyclo-dehydration stage is carried out by drop-by-drop addition of a cyclizing mixture that consists of triethylamine and acetic anhydride mixed in the synthesis solvent. The thus obtained polyimide is then precipitated in water and then ground. It is then filtered, rinsed, and then vacuum-dried in a furnace by gradually increasing the temperature until reaching 150° C.

The inherent viscosity of the polymer that is thus obtained is 1.3 dl/g.

The material in ground form is then put into solution in the DMAC at a mass concentration of 12% under the action of vigorous mechanical stirring at ambient temperature.

The clear solution is then filtered under a pressure of 0.2 MPa on a Millipore-type filter that has a cutoff threshold of 1 μm.

This solution is then shaped in the form of a film using a 300 μm spiraled bar on a glass plate that was previously degreased with acetone, and then dried.

The plate is inserted into a furnace. The evaporation of the solvent is carried out by a gradual elevation of the temperature up to 200° C. The final temperature is kept level for two hours. After cooling, the plate is immersed in water, where the separation of the film is observed.

After evaporation of the solvent, the film that is obtained has a mean thickness of 20 μm. A sample of this film was then tested in a circular permeation cell with an effective diameter of 5.5 cm placed in a thermostated chamber.

The upstream face of the thus tested membrane was flushed for 20 days with a gas flow of 10 Nl/h that consists of normal butane and isobutane or normal butene and isobutene, whereas the compartment downstream from the membrane, in which the permeate is collected, is flushed by a nitrogen flow of 1 Nl/h at atmospheric pressure.

The composition of the different fluids entering and exiting from the different compartments of the permeation cell is obtained by gas phase chromatography.

The sustained performance levels of the film, which remained constant for 20 days, are as follows:

TABLE 3

Performance Levels of the Polyimide 6FDA-BDAF
(Load Pressure = 0.15 MPa)

| Composition of the Feedstock | Temperature of the Film | Permeability of Normal Butane (or Normal Butene) | Mixture selectivity |
|---|---|---|---|
| Normal Butane/Isobutane (50/50) | 150° C. | 11 barrer | 8 |
| Normal Butene/Isobutene (50/50) | 150° C. | 14 barrer | 7 |

Example 2 (According to the Invention)

The synthesis of the polyimide film according to Example 2 is carried out in two stages. During the first stage, the 6FDA-type dianhydride is put into contact with the BDAF-type diamine in the N-methylpyrrolidone solvent (NMP) under inert atmosphere or in an anhydrous medium.

After 3 hours of stirring at ambient temperature, the acid polyamide is obtained. The second stage consists of a thermal dehydration of this acid polyamide by heating (30 minutes at 100° C., 1 hour at 160° C., 1 hour at 180° C., and two hours at 200° C.).

The thus obtained polyimide is then precipitated in water, ground, and dried as described in Example 1 of this invention. The inherent viscosity of the thus obtained polymer is 0.55 dl/g.

The polymer is then dissolved again in the solvent NMP at a mass concentration of 10%. The clear solution is then filtered under a pressure of 0.2 MPa on a Millipore-type filter that has a cutoff threshold of 1 μm.

This solution is then put into the form of a film using a 300 μm spiraled bar on a glass plate that was previously degreased with acetone, and then dried.

The plate is inserted into a furnace. The evaporation of the solvent is carried out by a gradual elevation of the temperature up to 200° C.

After evaporation of the solvent, the film that is obtained has a mean thickness of 32 μm. The performance levels of the film according to Example 2 have been obtained under test conditions that are identical to those described in Example 1.

TABLE 4

Performance Levels of the Polyimide 6FDA-BDAF
(Load Pressure = 0.15 MPa)

| Composition of the Feedstock | Temperature of the Film | Permeability of Normal Butane (or Normal Butene) | Mixture selectivity |
|---|---|---|---|
| Normal Butane/Isobutane (50/50) | 150° C. | 0.4 barrer | 8 |
| Normal Butene/Isobutene (50/50) | 150° C. | 0.6 barrer | 7 |

Example 3 (According to the Invention)

The polymer BTDA-BDAF that is the object of Example 3 is the result of the polycondensation of the 3,3',4,4'-benzophenonetetracarboxylic acid dianhydride (BTDA) and the 9,9'bis-(4-aminophenyl)fluorene diamine (BDAF) in an equimolar mixture.

After purification of the monomers by recrystallization in appropriate solvents, the polycondensation of the BTDA-BDAF polyimide is carried out in two stages: in a first step, the acid polyamide is produced, and then the polyimide is obtained in a second cyclization stage by a chemical method.

During the first polymerization stage, the mixing of the dianhydride and the diamine is carried out under inert atmosphere and in an anhydrous environment in the solvent NMP.

The cyclo-dehydration stage is carried out by drop-by-drop addition of a cyclizing mixture that consists of triethylamine and acetic anhydride mixed in the synthesis solvent. The thus obtained polyimide is then precipitated in water and then ground. It is then filtered, rinsed, and then vacuum-dried in a furnace by gradually increasing the temperature until reaching 150° C. The inherent viscosity of the thus obtained polymer was 0.8 dl/g in the NMP.

The material in ground form is then put into solution in the NMP at a mass concentration of 10% under the action of vigorous mechanical stirring at ambient temperature. The clear solution is then filtered under a pressure of 0.2 MPa on a Millipore-type filter that has a cutoff threshold of 1 μm.

This solution is then put in the form of a film using a 300 w spiraled bar on a glass plate that was previously degreased with acetone and then dried.

The plate is inserted into a furnace. The evaporation of the solvent is carried out by a gradual elevation of the temperature up to 200° C. The final temperature is kept level for two hours. After cooling, the plate is immersed in water, where the separation of the film is observed.

After evaporation of the solvent, the film that is obtained has a mean thickness of 24 μm. The performance levels of the film according to Example 4 have been obtained under test conditions that are identical to those that are described in Example 1.

TABLE 5

Performance Levels of the Polyimide Film BDTA-BDAF
(Load Pressure = 0.15 MPa)

| Composition of the Feedstock | Temperature of the Film | Permeability of Normal Butane (or Normal Butene) | Mixture selectivity |
|---|---|---|---|
| Normal Butane/Isobutane (50/50) | 150° C. | 2 barrer | 8 |
| Normal Butene/Isobutene (50/50) | 150° C. | 2.5 barrer | 8 |

Example 4 (According to the Invention)

The polymer BPDA-BDAF that is the object of Example 4 is the result of the polycondensation of the 3,3',4,4'-biphenyltetracarboxylic acid dianhydride (BPDA) and the 9,9'-bis-(4-aminophenyl)-fluorene diamine (BDAF) in an equimolar mixture.

The monomers are introduced into the solvent DMAC under inert atmosphere and in an anhydrous medium.

After 8 hours of stirring at ambient temperature, the acid polyamide is obtained. The second stage consists of a thermal dehydration of this acid polyamide by heating (for one hour at 100° C., three hours at 200° C.).

After evaporation of the solvent, the film that is obtained has a mean thickness of 40 μm.

The performance levels of the film as obtained according to Example 4 have been obtained under test conditions that are identical to those described in Example 1.

TABLE 6

Performance Levels of the Polyimide BDTA-BDAF
(Load Pressure = 0.9 MPa)

| Composition of the Feedstock | Temperature of the Film | Permeability of Normal Butane (or Normal Butene) | Mixture Selectivity |
|---|---|---|---|
| Normal Butane/Isobutane (50/50) | 150° C. | 0.2 barrer | 10 |
| Normal Butene/Isobutene (50/50) | 150° C. | 0.23 barrer | 8 |

Example 5 (Example According to the Invention)

A composite membrane that offers a selective layer according to the method that is described in this invention was synthesized by inducing hollow fibers of phenylene polyoxide produced by the Parker Filtration Company (Parker Hannifin SA, UCC France, Rue Albert Calmette, P.O. Box 6, 41260 La Chaussée St. Victor, France) according to the following method:

The polymer of type 6FDA-BDAF that is obtained according to the method described in Example 2 is put into solution in the NMP at a mass concentration of 5% under the action of vigorous mechanical stirring at ambient temperature.

The clear solution is then filtered under a pressure of 0.2 MPa on a Millipore-type filter that has a cutoff threshold of 1 μm. The poly-2,6-dimethyl-1,4-phenylene oxide fiber is quenched in the diluted polymer solution, and then it is extracted vertically from the solution by taking care that excess solution is evacuated by gravity.

The coated fiber is then put out to dry vertically in a study under an inert atmosphere according to the following thermal progression: 30 minutes at 100° C., 2 hours at 160° C.

Samples of coated fibers analyzed by scanning electronic microscopy showed that the selective polyimide layer in olefins had a thickness of between 0.1 and 0.5 μm.

A fiber bundle was then set in a calender with the epoxy resin and was subjected to tests for separation of the normal butane/isobutane mixture in the gaseous state under the conditions that are described in Example 1.

During the tests for separation of mixtures that consist of normal butane and isobutane at respective molar ratios of 50% and 50%, at a temperature of 150° C., and pressures upstream and downstream from the membrane respectively of 0.15 and 0.1 MPa, the mixture selectivity of the composite fibers was 8.

The invention claimed is:

1. A process for membrane separation of hydrocarbons, comprising subjecting to a membrane and selectively extracting a linear hydrocarbon that is contained in a mixture that comprises at least said linear hydrocarbon and a corresponding branched hydrocarbon, whereby the membrane has a selective layer comprising a dense polymer film whose chemical structure contains a bis-phenyl-9,9-fluorene group, in which the selective layer of the polymer membrane that contains the bis-phenyl-9,9-fluorene group is selected from the group that consists of polymers of the following families: polyimides, polyamides, polycarbonates, polysulfones, poly(amide imides), poly(ether sulfones), polyesters, or copolymers or polymer mixtures of these families.

2. The process for membrane separation according to claim 1, in which the selective layer of the polymer membrane that contains the bis-phenyl-9,9-fluorene group belongs to the family of polyimides.

3. The process for membrane separation according to claim 1, in which the selective layer of the polymer membrane that contains the bis-phenyl-9,9-fluorene group belongs to the family of polyamides.

4. The process for membrane separation according to claim 1, in which the selective layer of the polymer membrane that contains the bis-phenyl-9,9-fluorene group belongs to the family of polycarbonates.

5. The process for membrane separation according to claim 1, in which the selective layer of the polymer membrane that contains a bis-phenyl-9,9-fluorene group belongs to the family of polysulfones.

6. The process for membrane separation according to claim 2, in which the selective layer of the membrane is a polyimide that has been synthesized with the 2,2-bis(3,4-dicarboxyphenyl)hexafluoropropanoic acid dianhydride.

7. The process for membrane separation according to claim 2, in which the selective layer of the membrane is a polyimide that has been synthesized with the 3,3', 4,4'-biphenyltetracarboxylic acid dianhydride.

8. The process for membrane separation according to claim 2, in which the selective layer of the membrane is a polyimide that has been synthesized with the 3,3', 4,4'-benzophenonetetracarboxylic acid dianhydride.

9. The process for membrane separation according to claim 2, in which the selective layer of the membrane is a polyimide that has been synthesized with the 1,3-diamino-2,4,6-trimethylbenzene diamine.

10. The process for membrane separation according to claim 2, in which the selective layer of the membrane is a polyimide that is obtained from the polycondensation of the 2,2-bis(3,4-dicarboxyphenyl)hexa-fluoropropanoic acid dianhydride and the 9,9-bis(4-aminophenyl)fluorene diamine.

11. The process for membrane separation according to claim 2, in which the selective layer of the membrane is a polyimide that is obtained from the polycondensation of the 3,3', 4,4'-biphenyltetracarboxylic acid dianhydride and the 9,9-bis(4-aminophenyl) fluorene diamine.

12. The process for membrane separation according to claim 2, in which the selective layer of the membrane is a polyimide that is obtained from the polycondensation of the 3,3', 4,4'-benzophenone-tetracarboxylic acid dianhydride and the 9,9-bis (4-aminophenyl)fluorene diamine.

13. The process for membrane separation according to claim 1, in which the linear and branched hydrocarbon that are to be separated contain 4 carbon atoms.

14. The process for membrane separation according to claim 1, in which the linear and branched hydrocarbon that are to be separated contain 5 carbon atoms.

15. The process for membrane separation according to claim 1, in which the linear and branched hydrocarbon that are to be separated contain 6 carbon atoms.

16. The process for membrane separation according to claim 1, in which the selective membrane is deposited on the surface of a hollow-fiber-type substrate that is based on poly-2,6-dimethyl-1,4-phenylene oxide.

17. The process for membrane separation according to claim 1, in which the temperature of said process is encompassed between 40° C. and 200° C., and the pressure of the mixture that is to be separated is between 1 and 40 bar.

18. The process for membrane separation according to claim 1, in which the temperature of said process is between 50° C. and 150° C., and the pressure of the mixture that is to be separated is between 1 and 20 bar.

19. A process for membrane separation of hydrocarbons, comprising subjecting to a membrane a mixture of n-butane and isobutane or n-butene and isobutene, whereby the membrane has a selective layer comprising a dense polyimide film containing a bis-phenyl -9, 9-fluorine group, and selectively extracting n-butane or n-butene.

* * * * *

UNITED STATES PATENT AND TRADEMARK OFFICE
CERTIFICATE OF CORRECTION

PATENT NO. : 8,506,814 B2 Page 1 of 1
APPLICATION NO. : 12/376807
DATED : August 13, 2013
INVENTOR(S) : Gonzalez et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1223 days.

Signed and Sealed this
Fifteenth Day of September, 2015

Michelle K. Lee
*Director of the United States Patent and Trademark Office*